United States Patent [19]

Conrad et al.

[11] 4,271,047

[45] Jun. 2, 1981

[54] HYDROGENATED INDENOPYRANS AND THEIR USE IN AROMATIC COMPOSITIONS

[75] Inventors: Jens Conrad, Hilden; Horst Upadek, Erkrath; Klaus Bruns, Krefeld-Traar, all of Fed. Rep. of Germany

[73] Assignee: Henkel Kommanditgesellschaft auf Aktien, Düsseldorf-Holthausen, Fed. Rep. of Germany

[21] Appl. No.: 105,254

[22] Filed: Dec. 19, 1979

[30] Foreign Application Priority Data

Jan. 8, 1979 [DE] Fed. Rep. of Germany ....... 2900421

[51] Int. Cl.[3] ...................... C07D 311/78; C11B 9/00; A61K 7/46

[52] U.S. Cl. .............................. 252/522 R; 260/345.2

[58] Field of Search .................. 260/345.2; 252/522 R

[56] References Cited

U.S. PATENT DOCUMENTS 4,146,506 3/1979 Bruns et al. ...................... 252/522 R

OTHER PUBLICATIONS

Descotes et al., Tetrahedron Letters, 39, 3395 (1969).

*Primary Examiner*—Nicky Chan

*Attorney, Agent, or Firm*—Hammond & Littell, Weissenberger and Muserlian

[57] ABSTRACT

This invention is directed to compounds of the formula

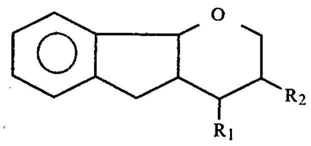

wherein $R_1$ and $R_2$ are each independently hydrogen or a methyl radical, with the proviso that only one of $R_1$ and $R_2$ is methyl radical, as well as to aromatic compositions containing said compounds and the use of such aromatic compositions to impart desired odors.

8 Claims, No Drawings

HYDROGENATED INDENOPYRANS AND THEIR USE IN AROMATIC COMPOSITIONS

FIELD OF THE INVENTION

This invention is directed to hydrogenated indenopyrans. More particularly, this invention is directed to hydrogenated indenopyrans and their use in aromatic compositions.

OBJECT OF THE INVENTION

It is the object of this invention to provide hydrogenated indenopyrans.

It is also an object of this invention to provide for the use of hydrogenated indenopyrans in aromatic compositions.

These and other objects of the invention will become more apparent in the discussion below.

DESCRIPTION OF THE INVENTION

It has been surprisingly found that compounds of the formula

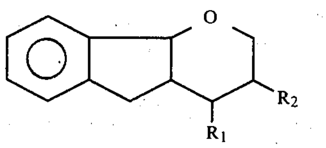
(I)

wherein $R_1$ and $R_2$ each independently represent hydrogen or a methyl radical, with the proviso that only one of $R_1$ and $R_2$ can be a methyl radical, can be prepared. It has also been found that these 2,3,4,4aβ,5,9bβ-hexahydroindeno[1,2-b]-pyrans of Formula I can be used as aromatics or in aromatic compositions.

The compounds of Formula I can be prepared by hydrogenation of the corresponding 4,4aβ,5,9bβ-tetrahydroindeno-[1,2-b]-pyrans of the formula

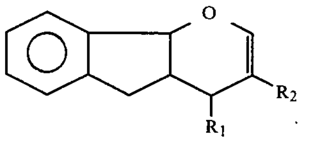
(II)

wherein $R_1$ and $R_2$ are as defined above, in the presence of a catalyst such as palladium on charcoal and at a temperature of approximately 175° C. and a pressure of about 50 to 150 bars. In an expedient embodiment of the preparation procedure, the hydrogenation takes place in a suitable anhydrous solvent, preferably an alkane. Useful alkanes would include those having from about 1 to 10 carbon atoms. The formation of by-products is almost completely suppressed under the hydrogenation conditions described.

The preparation of the tetrahydroindenopyrans of Formula II used as starting materials is carried out according to processes known from the literature, by the Diels-Alder reaction of indene with arcolein, methacrolein, or crotonaldehyde, as described in detail by G. Descotes and A. Jullien in Tetrahedron Letters, No. 39, pp. 3395-98, 1969.

Hexahydroindenopyrans useful according to the invention are (a) 2,3,4,4aβ,5,9bβ-hexahydroindeno-[1,2-b]-pyran;

(b) 4-methyl-2,3,4a$\beta$,5,9b$\beta$-hexahydroindeno-[1,2-b]-pyran; and (c) 3-methyl-2,3,4,4a$\beta$,5,9b$\beta$-hexahydroindeno-[1,2-b]- pyran.

Of the greatest importance is 2,3,4a$\beta$,5,9b$\beta$-hexahydroindeno-[1,2-b]-pyran, because of its interesting scent and ready accessibility.

The hexahydroindeno-[1,2-b]-pyrans to be used according to the invention are valuable fragrances, i.e., aromatics, with a very intensive odor of a cabbage-like indole note interesting to the perfumer. A special advantage of the aromatics according to the invention is their good ability to combine into novel and interesting aromatic nuances.

The hexahydroindenopyrans to be used as aromatics according to the invention can be mixed with other aromatics or fragrances, in the most varied ratios, to form new aromatic compositions. In general, the proportion of the hexahydroindenopyrans in the aromatic compositions will vary from about 0.1 to 20% by weight, based on the weight of the total composition. The remainder of the aromatic compositions will comprise customary constituents of aromatic or perfuming compositions. Such compositions can serve directly as perfume or as perfuming agents in cosmetics such as cremes, lotions, scented water, aerosols, toilet soaps, technical products such as detergents and cleansing agents, softeners, disinfectants, products for the treatment of textiles, and the like. To perfume the various products, the perfume compositions containing the mixtures according to the invention are added to the products generally in concentrations of from about 0.01 to 5 percent by weight, based on the weight of the products.

The following examples are intended to illustrate the subject of the invention and are not to be construed as limiting the invention thereto.

EXAMPLE I

Preparation of 2,3,4,4aβ,5,9bβ-Hexahydroindeno-[1,2-b]-Pyran

The compound 4,4aβ,5,9bβ-tetrahydroindeno-[1,2-b]-pyran, which had been prepared from indene and acrolein by the Diels-Alder reaction, served as starting material.

An amount of 29.5 g (0.17 mol) of 4,4aβ,5,9bβ-tetrahydroindeno-[1,2-b]-pyran, 20 ml of n-hexane, and 0.3 g of palladium on charcoal were heated in the stirrer autoclave under 50 bars hydrogen pressure for 4 hours at 175° C. Subsequently, the mixture was allowed to continue to react for 1 hour at 175° C. and an elevated hydrogen pressure of 150 bars and was then cooled, and afterwards the product was separated from the catalyst and distilled under vacuum. The yield was 25.3 g, (i.e., 85% of the theoretical yield) of 2,3,4,4aβ,5,9bβ-hexahydroindeno-[1,2-b]-pyran, which had a boiling point of 82° C. at 0.0133 mbar and a refractive index of $n_D^{20}=1.5488$.

Characteristic H-NMR-signals: $\delta=3.57$ ppm (m, 2H,—O$\underline{CH_2}$—); 4.83 ppm (d, J=5 Hz, 1H, $\underline{CH}$—O—); 7.23 ppm (m, 4H, aryl-H).

The product had an intensive cabbage-like indole note.

EXAMPLES II-III

In accordance with procedures analogous to that described in Example I, the compounds 3-methyl-2,3,4,4aβ,5,9bβ-hexahydroindeno-[1,2-b]-pyran and 4-methyl-2,3,4,4a$\beta$,5,9b$\beta$-hexahydroindeno-[1,2-b]-pyran, which each possess a similar cabbage-like indole note of lower intensity, can be prepared from the corresponding tetrahydroindeno-[1,2-b]-pyrans that can be obtained by the Diels-Alder reaction from indene with methacrolein or crotonaldehyde.

EXAMPLE IV

Jasmine Base

| Component | Parts by weight |
|---|---|
| 2,3,4,4a$\beta$,5,9b$\beta$-Hexahydroindeno-(1,2-b)-pyran | 10 |
| Benzylacetate | 300 |
| Benzyl alcohol | 300 |
| Ylang-ylang oil | 100 |
| Linalool | 75 |
| $\alpha$-Amylcinnamic aldehyde | 75 |
| Linalyl acetate | 50 |
| Methyl anthranilate | 25 |
| Benzylbenzoate | 65 |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A compound of the formula

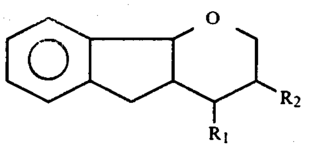

wherein $R_1$ and $R_2$ are each independently hydrogen or a methyl radical, with the proviso that only one of $R_1$ and $R_2$ is a methyl radical.

2. The compound of claim 1 which is 2,3,4,4a$\beta$,5,9b$\beta$-hexahydroindeno-[1,2-b]-pyran.

3. An aromatic composition consisting essentially of from about 0.1 to 20% by weight, based on the total weight of the composition, of a compound of claim 1 and the remainder customary constituents of aromatic compositions.

4. A process for imparting a desired odor to a product comprising the step of adding to said product a sufficient amount of the aromatic composition of claim 3 to provide the desired odor.

5. An aromatic composition consisting essentially of from 0.1 to 20% by weight, based on the total weight of the composition, of a compound of claim 2 and the remainder customary constituents of aromatic compositions.

6. A process for imparting a desired odor to a product comprising the step of adding to said product a sufficient amount of the aromatic composition of claim 5 to provide the desired odor.

7. A process for imparting a cabbage-like indole note to a product comprising the step of adding to said product a sufficient amount of the aromatic composition of claim 3 to provide the cabbage-like indole note.

8. A process for imparting a cabbage-like indole note to a product comprising the step of adding to said product a sufficient amount of the aromatic composition of claim 5 to provide the cabbage-like indole note.

* * * * *